United States Patent [19]

Cantrell

[11] Patent Number: 5,137,689
[45] Date of Patent: Aug. 11, 1992

[54] METHOD AND APPARATUS FOR CLEANING INSTRUMENTS

[76] Inventor: Stephen B. Cantrell, 3441 N. Druid Hills Rd., Apt. M, Atlanta, Ga. 30033

[21] Appl. No.: 68,538

[22] Filed: Jul. 1, 1987

[51] Int. Cl.$^5$ ............................................. A61L 2/00
[52] U.S. Cl. ................................. 422/28; 422/37; 422/294; 422/300; 422/305
[58] Field of Search ................... 422/27–29, 422/37, 294, 300, 305

[56] References Cited

U.S. PATENT DOCUMENTS

| | | | |
|---|---|---|---|
| 2,491,015 | 12/1949 | Poole | 422/28 |
| 3,963,438 | 6/1976 | Banet | 422/37 |
| 4,262,799 | 4/1981 | Perrett | 422/300 |
| 4,299,244 | 11/1981 | Hirai | 134/170 |
| 4,496,522 | 1/1985 | McConnell | 422/300 |
| 4,517,702 | 5/1985 | Jackson | 15/114 |

*Primary Examiner*—Robert J. Warden
*Assistant Examiner*—Lyle A. Alexander
*Attorney, Agent, or Firm*—Patrick F. Henry, Sr.

[57] ABSTRACT

Pressurized liquid is forced through the instrument simultaneous with submerging in a container of disinfectant or sterilization solution and also a gas may be introduced. The containers of the solutions receive the instrument which is mounted to be driven from one container to another, selectively by electric motors which are controlled through an electrical circuit that also operates pumps and valves in a pre-determined sequence of operations.

12 Claims, 4 Drawing Sheets

METHOD AND APPARATUS FOR CLEANING INSTRUMENTS

There is disclosed the disinfection and/or sterilization of instruments, such as air-driven dental drills, hoses and other devices which are used in medicine or dentistry. The instrument is moved into and out of the solution by electrical-driven motors and a solution is pumped through the instrument by means of pumps and valves.

Autoclaving is a well-known procedure for sterilizing instruments for use in medicine or dentistry. However, some instruments such as air-driven dental drills and hoses cannot withstand the autoclaving process. Manual exterior washing with a commercially available disinfectant, such as glutaraeldehyde or alcohol, is not always practical or effective. The anxiety of a patient must be considered with respect to serious disease such as AIDS (Acquired Immune Deficiency Syndrome) and precautions must be taken to create a secure and comfortable atmosphere in an effort not only to prevent cross-contamination between patients, but to take precautions that are practical and positive in operation. Therefore, autoclaving or manual washing is not practical in some situations and professional offices. Manual washing does not force the solution inside instruments, such as air-driven dental drills and hoses. The dunking of such instruments in a solution is not sufficient. In the medical field of anesthesiology it is known to use disposable liners for hoses and instruments. However, such disposable liners have not been developed for use with air-driven dental drills and other instruments, which may have internal turbine engines turning at speeds up to 400,000 RPM.

There is therefore a critical need for a method of disinfecting and/or sterilizing certain instruments, such as air-driven dental drills, and for an apparatus which can be used in medical or dental offices and purchased and operated economically. The method comprises the induction of a liquid medium, under pressure, into all accessible mechanism of an instrument, such as a high-speed turbine dental hand piece and hoses. The instrument is submerged in the liquid medium and even in conjunction with or in alternation with the introduction of liquid, a gas may be introduced.

An object of this invention is to provide a simple and expedient way to disinfect and/or sterilize an instrument.

Another object of this invention resides in the particular method of submerging the instrument in a solution which is forced through the instrument and returned to the supply container for reuse and also an arrangement, whereby more than one solution may be used in more than one container. Also, the procedure may be practiced by a table top apparatus which is contained in a housing, somewhat like a copying machine, in which motors operate pumps by means of an electrical circuit controlled by an operator.

Other and further objects and advantages of this invention will become apparent upon reading the following description of a preferred embodiment taken in conjunction with the accompanying drawings, in which.

DESCRIPTION OF A PREFERRED EMBODIMENT

Figure 1:
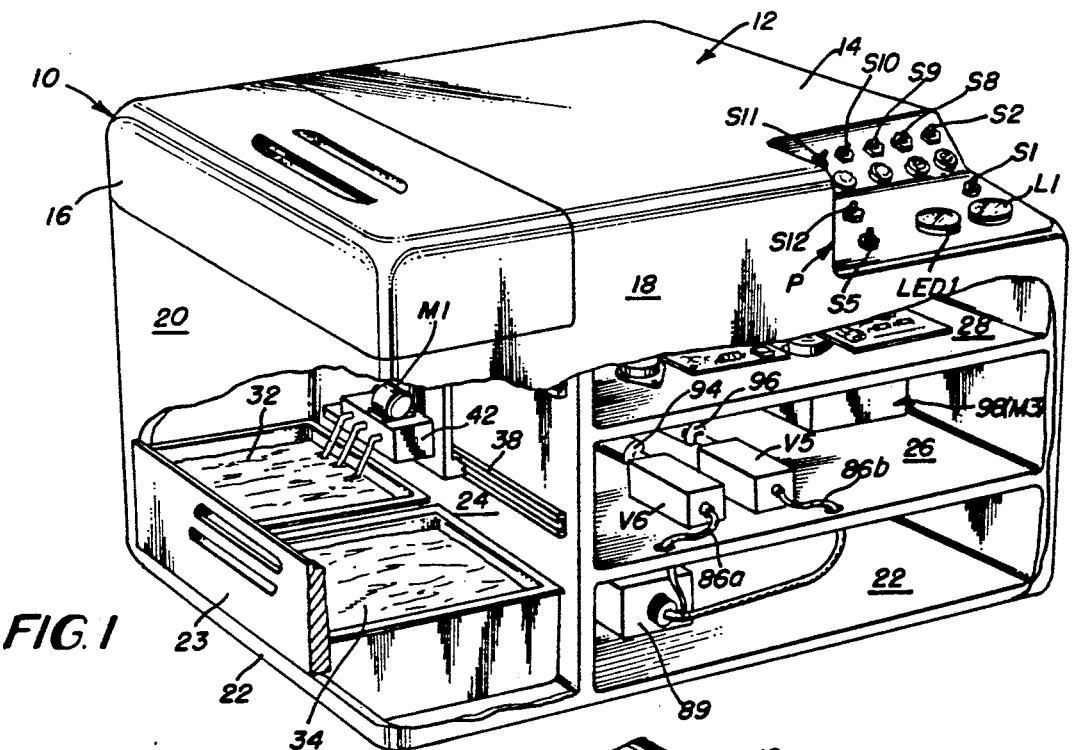
FIG. 1 is a perspective view of the apparatus with part of the housing broken away, showing the internal detail.

The apparatus 10 is contained within a housing or cabinet 12 (constructed from molded plastic, stainless steel or the like, somewhat similar to a copying machine) having a top 14, a removable end cover 16, sides 18, ends 20, bottom 22 and a removable basin compartment cover 23. The interior of the cabinet 12 is divided vertically by wall 24 and horizontally by shelves 26 and 27. First and second liquid containers 28, 30 are supported on the bottom 22 on one side of the vertical wall 24 to contain respective liquid solutions 32 for disinfection and 34 for sterilization. Any well-known solution may be used for disinfection and/or sterilization such as a glutaraeldehyde mixture or a commercially available alcohol.

Figure 2:
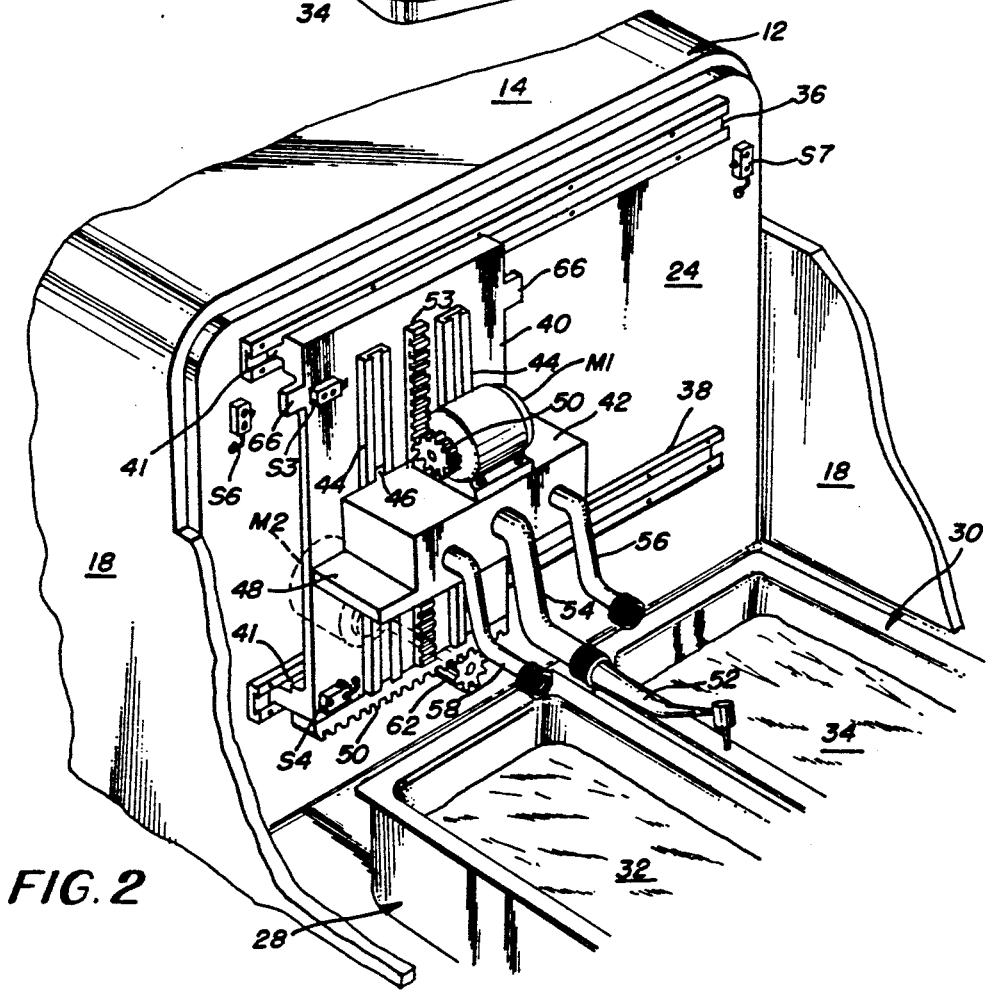
FIG. 2 is a perspective view of a portion of the apparatus shown in FIG. 1 with parts broken away.
Figure 3:
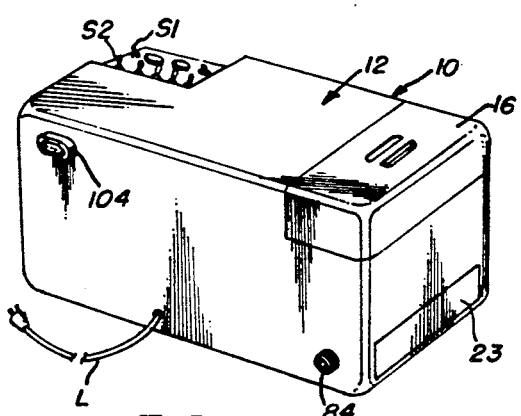
FIG. 3 is a perspective view of the apparatus housing from a rear view.
Figure 4:
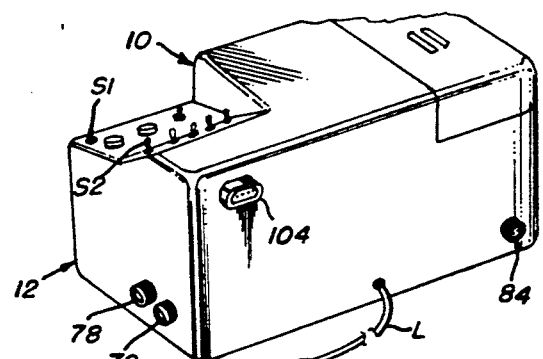
FIG. 4 is a perspective view similar to the one in FIG. 3 but from a different angle.
Figure 8:
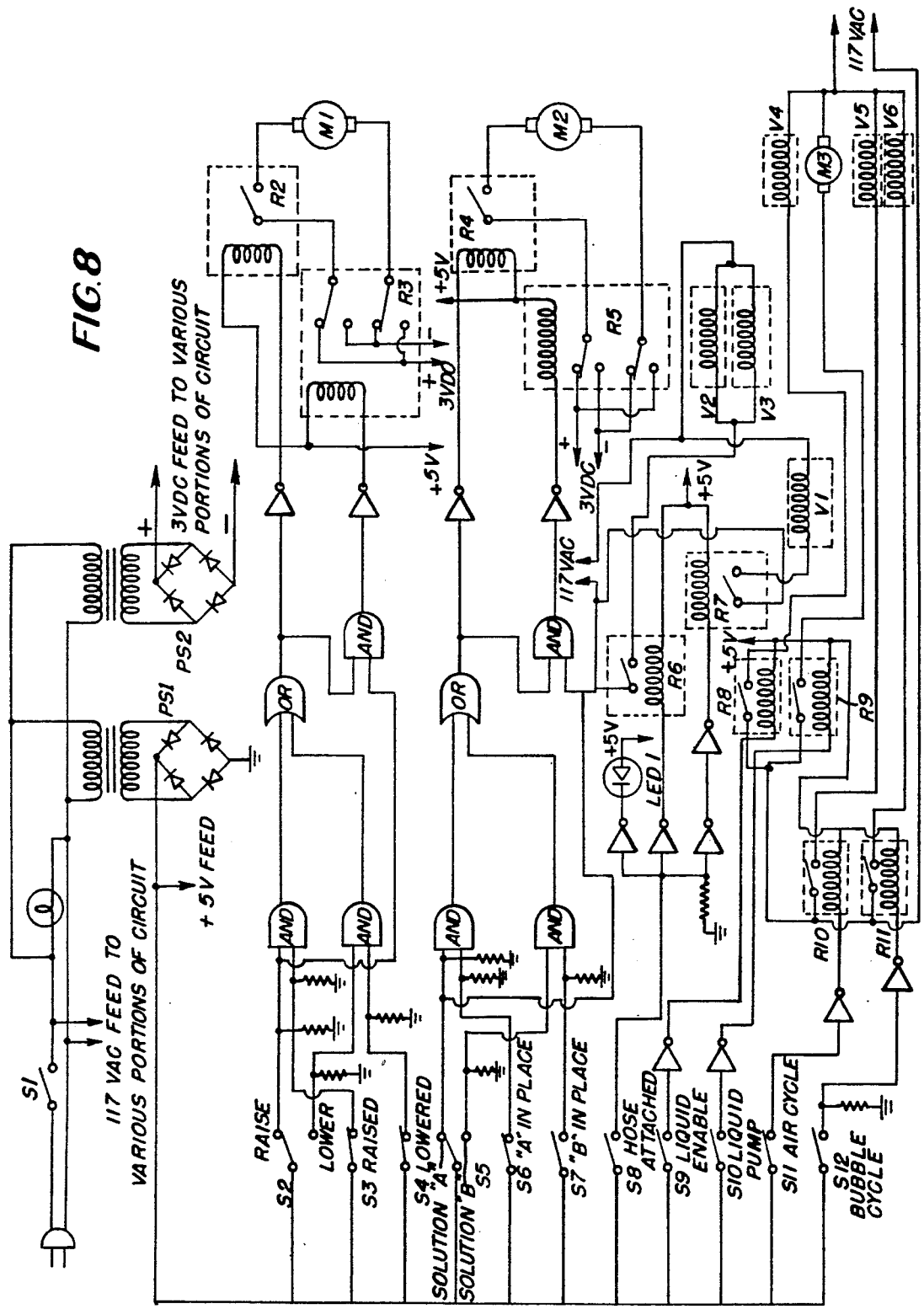
FIG. 8 is a circuit diagram of the circuitry and components on the apparatus of FIGS. 1 through 6.

A pair of spaced, dove-tailed guide bars 36, 38 mounted on wall 24 provide a dove-tailed track in which is mounted a traveling plate 40 having a top and bottom dove-tail member 41 which fits in the respective dove-tailed track bar 36, 38 in the manner shown in FIG. 1 and 2. A vertically movable motor support 42 is mounted in spaced, opposed dove-tail guide bars 44 in which are fitted complementary dove-tail members 46 attached to support 42. A switch actuator 48 protrudes from support 42. A synchron reversible motor M 1 is mounted on support block 42 and rotates a pinion 50 operating in a vertically disposed, straight rack 51 mounted between the vertical dove tail guide bars 44 so that the support block 42 is selectively driven upwardly or downwardly to raise and lower a typical dental instrument 52 such as an air-driven drill selectively attached to a tube fitting or receptacle 54 carried by block 42. Other open fittings 56 and 58 are also carried by support 42. There are switches S 1 through S 12 to be referred to later (FIG. 8). In the normal travel from bottom to top or vice versa switch actuator 48 contacts a switch S 3 at the top and a switch S 4 at the bottom to limit the travel in a respective direction and to stop the operation of motor M 1.

Also carried by plate 40 is a straight rack 60 driven by pinion 62 mounted on a motor M 2 which is mounted on the wall 24. Plate 40 has switch actuators 66 for contacting switches S 6 and S 7 to limit travel from left to right and vice versa and to actuate and stop the operation of motor M 2 accordingly. Therefore, in the operation of the respective motors M 1, M 2 the instrument 52 is caused to travel selectively from solution 32 in which it is immersed to solution 34 in which it is immersed, or if desired only to one or the other of said solutions 32, 34.

Figure 5:
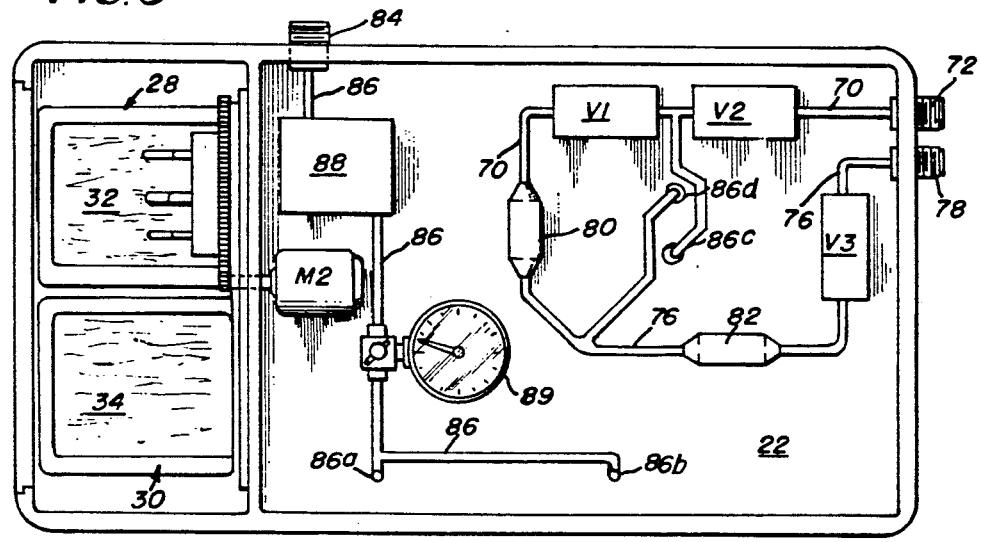
FIG. 5 is a plan view of the components on one shelf level of the apparatus shown in FIGS. 1 and 2.

Referring to FIG. 5, the lower shelf 22 supports motor M 2 and solenoid valves V 1 and V 2 which is by conduit 70 to an external fitting 72. A solenoid valve V 3 is connected by conduit 76 to an external fitting 78. External fittings 72 and 78 are for use with each end, respectively, an optional instrument hose. Backflow valves 80, 82 are connected to respective solenoid valves V 1 and V 2. An external threaded connector 84 leads through conduit 86 to a particle filter and moisture trap 88, through conduit 86 to an air-pressure regulator 89 and from it through line 86 and through branches 86a, b to the corresponding lines on the level 26 above.

Figure 6:
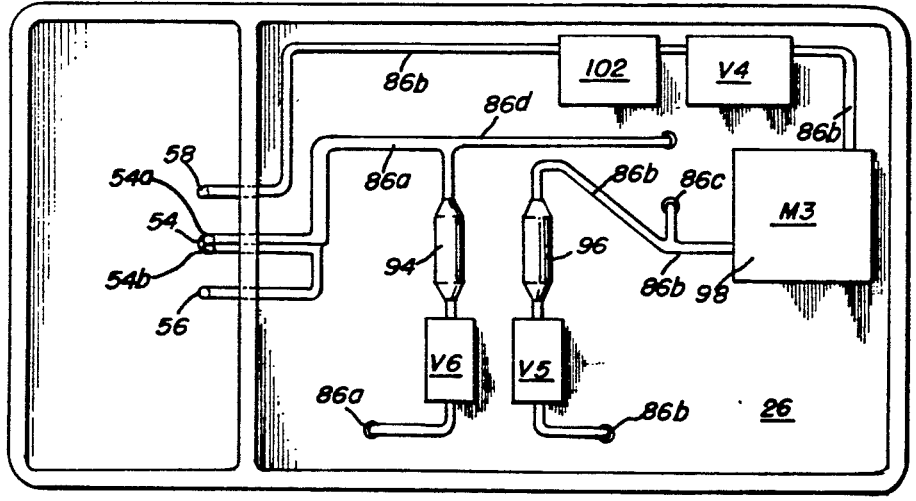
FIG. 6 is a plan view of components another shelf in the apparatus shown in FIG. 1.
Figure 7:
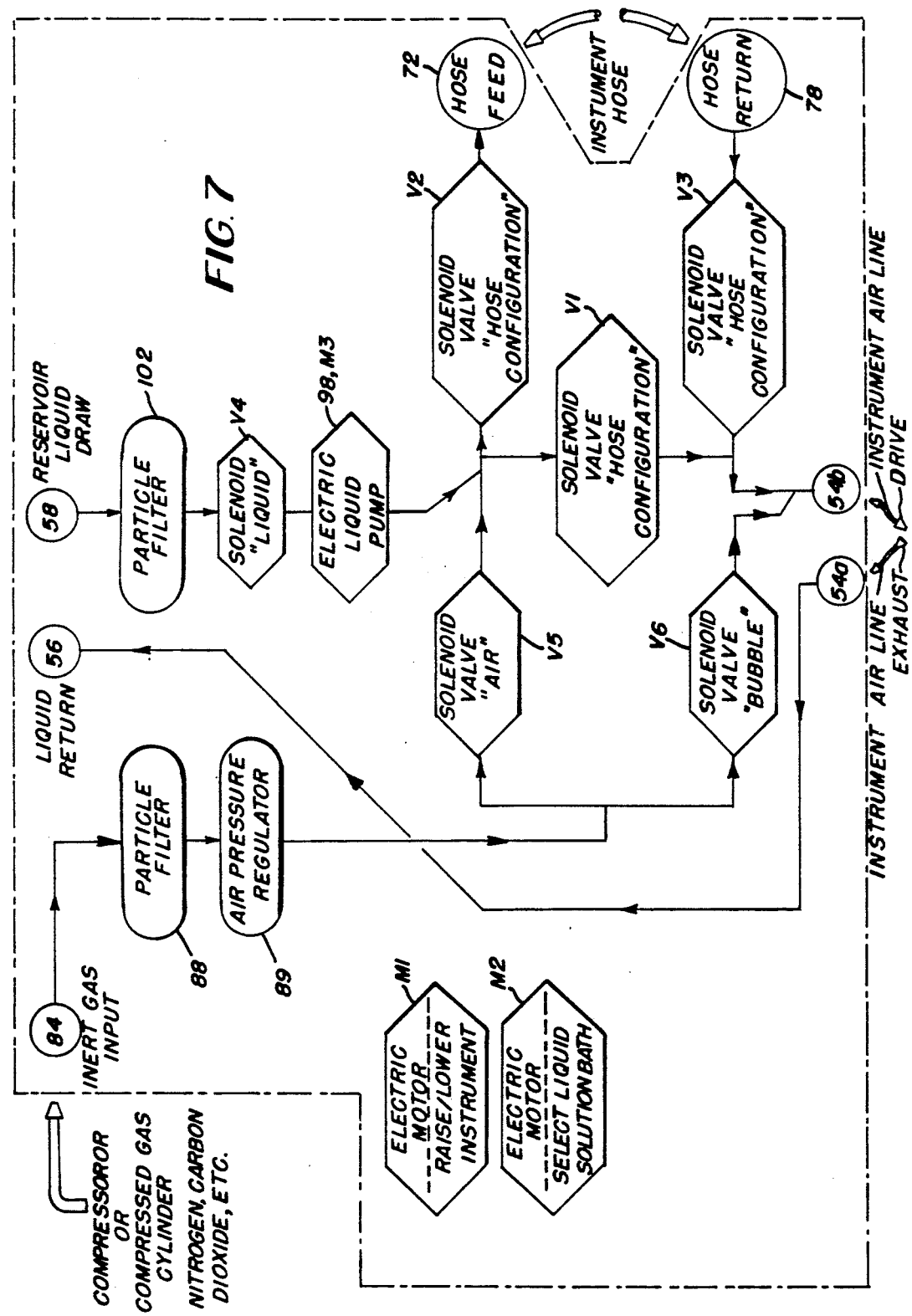
FIG. 7 is a flow diagram of the method and procedure accomplished by the apparatus shown in FIG. 1 through 6 inclusive.

Referring to FIG. 6, lines 86a and 86b from the bottom 22 continue to respective "bubble" solenoid valve V 5 and "air" solenoid valve V 6, each of which has connected thereto a respective backflow valve 94, 96. Valve 96 leads through line 86b which also receives the output from liquid pump 98 which comprises a motor M 3. Liquid pump 98 receives flow from fitting 58 (submerged in solution bath along with the instrument) via particle filter 102 and solenoid valve V 4. The gas or liquid flow through line 86d, along with the gas flow through solenoid valve V 6 and backflow valve 94, feed line 54a, which is coupled to the instrument. Return flow from the instrument enters line 54b and is re-deposited into the solution bath via line 56.

| COMPONENTS IN CIRCUIT DIAGRAM IN FIG. 8: | |
|---|---|
| LEGEND | DESCRIPTION |
| S 1 | Main power switch located on a front control panel P. |
| S 2 | Front panel switch to raise/lower the elevator arm. (Note: All switches serving as origins of 5 volt logic circuits are tied to chassis ground through bleeder resistors to prevent floating to a high logic state) |
| S 3 | Micro switch located at the top of the plate 40 normally closed, except when contacted by contact 48. |
| S 4 | Micro switch at bottom of plate 40 open only when contact by contact 48 is lowered. |
| S 5 | Disinfecting solution 32/34 selector switch, located on front panel. |
| S 6 | Mirco switch on basin selector sliding track normally closed, except when solution 32 is positioned beneath the instrument 52 |
| S 7 | Corresponding micro switch for solution 34. |
| S 8 | Front panel switch to be closed by operator if a hose is attached. |
| S 9 | Front panel switch, to be closed in order to allow liquid flow. |
| S 10 | Front panel switch to activate the liquid pump 98. |
| S 11 | Front panel switch to activate the "air" cycle through VS and backflow valve 96. |
| S 12 | Front panel switch to activate the "bubble" cycle through V6 and backlow valve 94. |
| L 1 | Front panel pilot lamp ("power on"). |
| LED 1 | Front panel indicator light to remind operator that a hose must be properly attached to prevent liquid spillage when the cycle begins. |
| PS 1 | 5 volt DC power supply, to drive logic circuits and relays R 2, 3, etc. |
| PS 2 | 3 volt DC power supply, to drive motors M 1, M 2. |
| R 3, 5 | Double pole double throw relays, 5 volt DC coils (to reverse motor spolarity). |
| M 1 | Elevator motor, 3 volts DC. |
| M 2 | A lateral motor, 3 volts DC. |
| M 3 | Pump 98 motor. |
| 104 | Computer receptacle. |
| L | 117 VAC line cord. |
| V 1, 2, 3 | "Hose configuration" solenoid valves, 117 volts AC. |
| V 4 | Liquid solenoid valve. |
| V 5 | Air solenoid valve. |
| V 6 | Bubble solenoid valve. |

OPERATION

The apparatus 10 is enabled by closing switch S 1, causing illumination of lamp L 1 and provides operating voltage to power supplies PS 1 and PS 2.

The operator attaches the air-driven instrument 52 to the instrument connector on the movable plate 40 which includes the "Instrument Feed" and "Instrument Return" channels 54a, 54b and fittings 56, 58. If an instrument hose (not shown) is to be included in the disinfection process, such a hose may be attached at the "Hose Feed" and "Hose Return" access connections at fittings 72, 78 if the hose is desired to be included. The operator closes switch S 8 which results in illumination of LED 1 (a reminder that a hose must be attached), closure of relay R 6. and opening of valves V 2 and V 3, thus allowing fluid to flow through a hose. Conversely, leaving switch S 8 open will result in closure of relay R 7 and opening of valve V 1, thus allowing fluid to bypass the hose connections and remain within the unit.

The operator begins the cycle by closing switch S 2 into the "Lower" position. Gating action in the logic circuit will cause closure of relay R 2 and activation of motor M 1, which will lower the instrument into the liquid bath. When the plate 40 has been lowered to the point that its bed contact opens switch S 4, the logic circuit opens relay R 2 and motor M 1 locks in the lowered position. At this point, the instrument 52 is submerged along with the "Reservoir Liquid Draw" fitting 58 and "Liquid Return" channel fitting 56.

The operator closes switch S 9 which causes closure of relay R 8 and opening of valve V 4. Thus providing an open course for liquid flow through the instrument 52. When switch S 10 is closed by the operator, closure of relay R 9 will activate motor M 3 and effect the pumping of liquid through the system. This state may continue as long as desired.

If desired during the liquid pumping cycle, the operator may choose to close switch S 12. This will close relay R 11 and open valve V 6, allowing a small stream of air bubbles (from an external source of compressed air or gas via coupling 84) to be introduced into the liquid in line 86a and subsequently coupling 54a just before it enters the instrument.

The liquid pumping cycle is completed by opening switches S 9 and S 10. The operator then closes switch S 11. This causes closure of relay R 10 and opening of valve V 5, allowing pressurized gas to flow through the system. As this continues, the operator closes switch S 2 to the "Raise" position. This causes the closure of relay R 2 and activation of motor M 1, just as in lowering. It also causes closure of relay R 3, thus reversing polarity to motor M 1 and causing it to drive the plate 40 in upward direction. The raising motion continues until the plate 40 opens switch S 3, thus opening relay R 1 and removing voltage from motor M 1. (Relay R 3 remains closed only as long as voltage is being applied to motor M 1, in order to conserve energy and relay life.)

This completes the cycle of operation. If the operator desires, the cycle may be repeated with the second solution of solutions 32, 34. To accomplish this, switch S 5 should be closed to the "Solution B" position. The operation of switch S 5 through its logic circuit controlling relay R 4 and motor M 2 is directly analogous to the sequence described for switch S 2 controlling relay R 2 and motor M 1. As solution 32 or 34 is selected by alternate settings of switch S 5, relay R 5 controls polarity of motor M 2 so that the plate 40 moves horizontally over the appropriate liquid bath. As in the vertical system, motion ceases when the plate 40 opens switch S 6 or switch S 7.

The cycle may be adjusted in length or repeated as desired. It is also apparent that the system of switches described could be replaced by an automatic timing device through a computer receptacle 104.

While I have shown and described a particular method and embodiment, this is my way of illustration only various changes may be made within the scope of my invention as detailed only by proper interpretation of the claims.

What is claimed:

1. A method of selectively cleaning an instrument with more than one solution, said instrument having at least one inside passage with parts therein, comprising: containing said solutions separately in separate containers to prevent mixing of said solutions, pressurizing selectively one of the selected said solutions by a fluid pump thereby forcing said solution under pressure through the inside passage in the instrument while submerging the instrument in the selected solution, selectively moving the instrument from one solution to another said solution, submerging the instrument in each of said solutions by attaching the instrument to a movable support, and moving said support to move said instrument into and out of a selected solution.

2. The method of claim 1, wherein: the solution is selected from the group consisting of sterilants and disinfectants.

3. The method in claim 1 wherein the instrument is moved both vertically and horizontally.

4. A method of selectively cleaning an instrument with a selected solution, said instrument having at least one inside passage with parts therein, comprising: pressurizing the selected solution and pumping said solution under pressure through the inside passage, forcing a pressurized gas, including air, under pressure through the inside passage of the instrument while the solution is being moved through the inside passage of the instrument and selectively until the solution is substantially removed from the instrument.

5. In an apparatus for cleaning an instrument selectively with more than one solution wherein said instrument has at least one inside passage with parts therein:
separate container means for more than one solution for selectively cleaning the inside passage, including the choice of a sterilizing and disinfecting solution,
a base for supporting said container means,
instrument support means movably mounted on said base for moving said instrument separately and selectively into and out of a selected solution,
conduit means on said support means for receiving said inside passage in closed communication whereby the solution may be forced through said inside passage,
fluid pump means for pressurizing and forcing said solution through the passage in said instrument under pressure, and
means for returning said solution to said container.

6. The device in claim 5, wherein there is a pump for forcing said solution under pressure through said instrument.

7. The device claimed in claim 5 wherein said means for moving said instrument comprises an instrument support member and electrical means for moving said support member vertically and horizontally from one solution to another.

8. The device claimed in claim 7 wherein there is an electrical motor for moving said instrument in a vertical direction and another electrical motor for moving said instrument in a horizontal direction.

9. The device in claim 8 including an electrical circuit being switch means therein, said motors having in said electrical circuit.

10. The device claim 9 wherein said switch means has manual switches on said device for operating said motors.

11. The device in claim 10 wherein said circuit includes electrical contact switches contacted during movement of said instrument to control the movement.

12. In an apparatus for cleaning an instrument selectively with a selected solution wherein said instrument has at least one inside passage with parts therein:
container means for the selected solution, which includes the choice of a sterilizing and disinfecting solution, for selectively cleaning the instrument,
a base for supporting said container means,
instrument support means movably mounted on said base for supporting said instrument selectively into and out of the selected solution,
conduit means on said support means for receiving said instrument in closed communication whereby the solution may be forced through the inside passage of said instrument,
means for forcing said solution through the inside passage of said instrument under pressure,
means for returning said solution to said container, and
means for delivering a gas, such as air, through the inside passage of said instrument under pressure to remove the selected solution from the instrument.

* * * * *